United States Patent
Jin

(10) Patent No.: US 9,318,708 B2
(45) Date of Patent: Apr. 19, 2016

(54) HOLE TRANSPORT MATERIAL FOR ORGANIC ELECTROLUMINESCENCE DEVICE AND ORGANIC ELECTROLUMINESCENCE DEVICE COMPRISING THE SAME

(71) Applicant: SAMSUNG DISPLAY CO., LTD., Yongin, Gyeonggi-Do (KR)

(72) Inventor: Xiulan Jin, Yongin (KR)

(73) Assignee: SAMSUNG DISPLAY CO., LTD., Yongin, Gyeonggi-do (KR)

( * ) Notice: Subject to any disclaimer, the term of this patent is extended or adjusted under 35 U.S.C. 154(b) by 0 days.

(21) Appl. No.: 14/087,314

(22) Filed: Nov. 22, 2013

(65) Prior Publication Data

US 2014/0155600 A1    Jun. 5, 2014

(30) Foreign Application Priority Data

Nov. 30, 2012 (JP) .................. 2012-263853

(51) Int. Cl.
| | | |
|---|---|---|
| *C07D 487/04* | (2006.01) | |
| *C07D 519/00* | (2006.01) | |
| *H01L 51/50* | (2006.01) | |
| *H01L 51/52* | (2006.01) | |
| *H01L 51/54* | (2006.01) | |
| *H05B 33/14* | (2006.01) | |
| *H01L 51/00* | (2006.01) | |

(52) U.S. Cl.
CPC .......... *H01L 51/0061* (2013.01); *C07D 487/04* (2013.01); *H01L 51/0065* (2013.01); *H01L 51/0072* (2013.01); *H01L 51/0073* (2013.01); *H01L 51/0074* (2013.01); *H01L 51/5056* (2013.01)

(58) Field of Classification Search
CPC .............. C07D 487/04; C07D 519/00; H01L 51/5032; H01L 51/5064; H01L 51/5296; H01L 51/0032; H05B 33/14
USPC .............. 548/418, 419; 257/40; 428/690, 917
See application file for complete search history.

(56) References Cited

U.S. PATENT DOCUMENTS

2011/0240968 A1    10/2011    Kim et al.

FOREIGN PATENT DOCUMENTS

| CN | 101161765 A | 4/2008 |
|---|---|---|
| EP | 0 906 948 A1 | 4/1999 |
| EP | 2 371 828 A1 | 10/2011 |
| JP | 2004-196716 A | 7/2004 |
| JP | 2004-203765 A | 7/2004 |
| KR | 10-2010-0131745 A | 12/2010 |
| KR | 10-2011-0079402 A | 7/2011 |
| KR | 10-2012-0009984 A | 2/2012 |
| KR | 10-2012-0092909 A | 8/2012 |
| WO | WO 2010/103765 A1 | 9/2010 |
| WO | WO 2012/015265 A1 | 2/2012 |
| WO | WO 2012026780 A1 * | 3/2012 |
| WO | WO 2012/091471 A2 | 7/2012 |

OTHER PUBLICATIONS

Lee et al. KR 2013096335, CA 159: 464782, 2013; CAPLUS Abstract provided.*

* cited by examiner

*Primary Examiner* — Venkataraman Balasubramanian
(74) *Attorney, Agent, or Firm* — Lee & Morse, P.C.

(57) ABSTRACT

A hole transport material for an organic electroluminescence device, the hole transport material being represented by the following Formula 1,

[Formula 1]

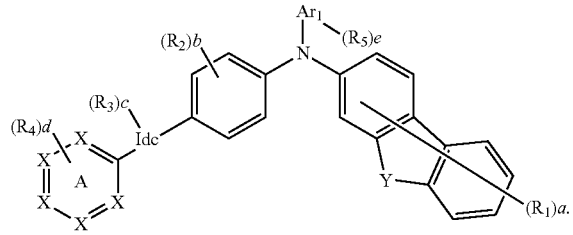

6 Claims, 1 Drawing Sheet

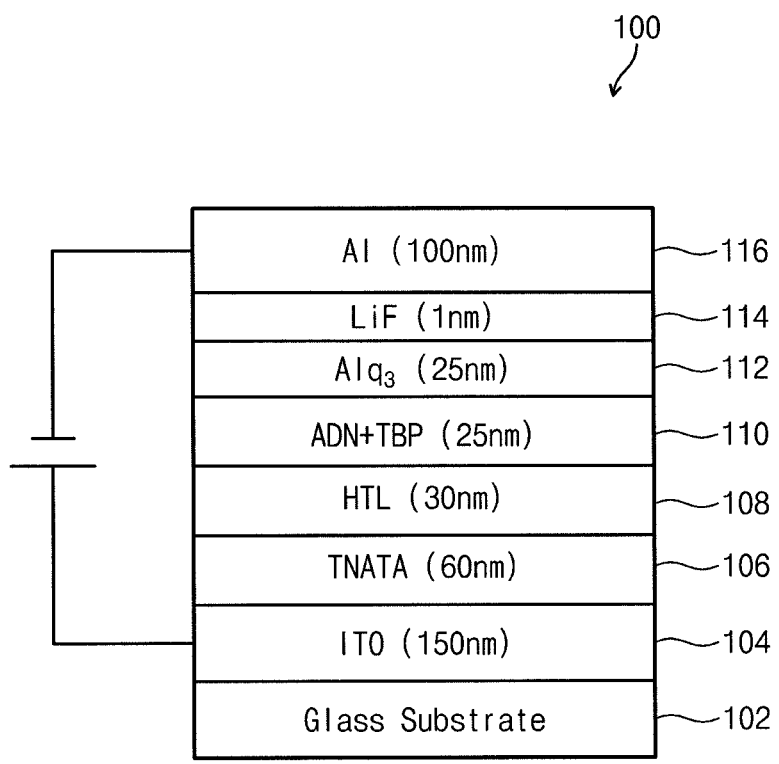

HOLE TRANSPORT MATERIAL FOR ORGANIC ELECTROLUMINESCENCE DEVICE AND ORGANIC ELECTROLUMINESCENCE DEVICE COMPRISING THE SAME

CROSS-REFERENCE TO RELATED APPLICATION

Japanese Patent Application No. 2012-263853, filed on Nov. 30, 2012, in the Japanese Patent Office, and entitled: "Hole Transport Material for Organic Electroluminescence Device and Organic Electroluminescence Device comprising the Same," is incorporated by reference herein in its entirety.

BACKGROUND

1. Field

Embodiments relate to a hole transport material for an organic electroluminescence device and an organic electroluminescence device using the same.

2. Description of the Related Art

In recent years, organic electroluminescence (EL) displays that are one type of image displays have been actively developed. Unlike a liquid crystal display and the like, the organic EL display is a so-called self-luminescent display that recombines holes and electrons injected from a positive electrode and a negative electrode in an emission layer to thus emit a light from a light-emitting material including an organic compound of the emission layer, thereby performing display.

SUMMARY

Embodiments are directed to a hole transport material for an organic electroluminescence device represented by compound (1) of following Formula 1,

[Formula 1]

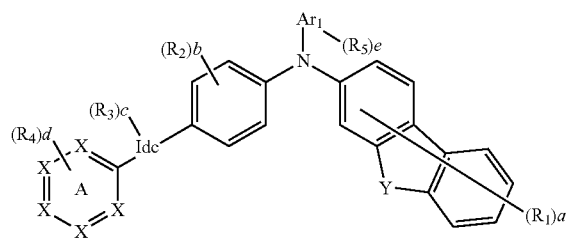

(1)

In Formula 1, Idc may be an indolocarbazole divalent group, each X may independently be a methine group or a nitrogen atom, Y may be a methylene group, an oxygen atom, or a sulfur atom, $Ar_1$ may be an aryl group having 6 to 20 carbon atoms, each of $R_1$-$R_5$ may independently represent a substituted or unsubstituted straight or branched chain alkyl group having 6 to 20 carbon atoms, or an aryl group or a heteroaryl group having 6 to 20 carbon atoms, a may be an integer of 0 to 9, b may be an integer of 0 to 4, c may be an integer of 0 to 10, d may be an integer of 0 to 5, and e may be an integer of 0 to 10.

The Idc may be a divalent one of compounds (2) to (7) of following Formula 2,

[Formula 2]

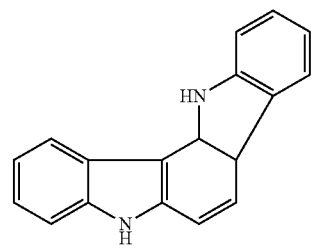

(2)

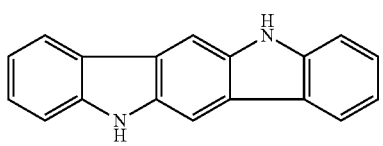

(3)

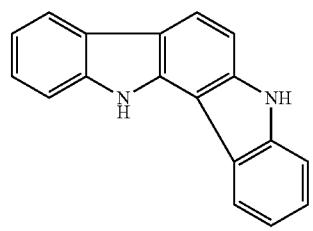

(4)

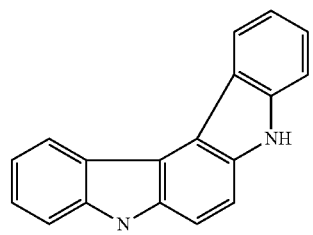

(5)

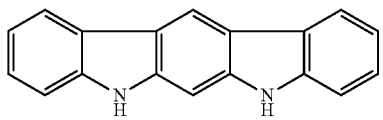

(6)

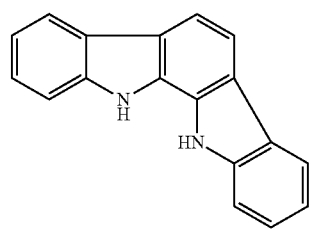

(7)

Ring A may include at least one nitrogen atom.

Embodiments are also directed to an organic electroluminescence device including a hole transport layer that includes a hole transport material represented by compound (8) of following Formula 3,

[Formula 3]

(8)

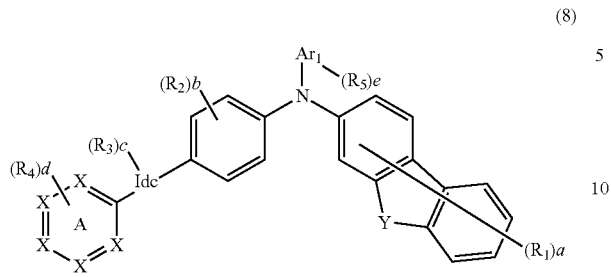

In Formula 3, Idc may be an indolocarbazole divalent group, each X of ring A may independently be a methine group or a nitrogen atom, Y may be a methylene group, an oxygen atom, or a sulfur atom, $Ar_1$ may be an aryl group having 6 to 20 carbon atoms, each of $R_1$-$R_5$ may independently represent a substituted or unsubstituted straight or branched chain alkyl group having 6 to 20 carbon atoms, or an aryl group or a heteroaryl group having 6 to 20 carbon atoms, a may be an integer of 0 to 9, b may be an integer of 0 to 4, c may be an integer of 0 to 10, d may be an integer of 0 to 5, and e may be an integer of 0 to 10.

The Idc may be a divalent one of compounds (9) to (14) of following Formula 4,

[Formula 4]

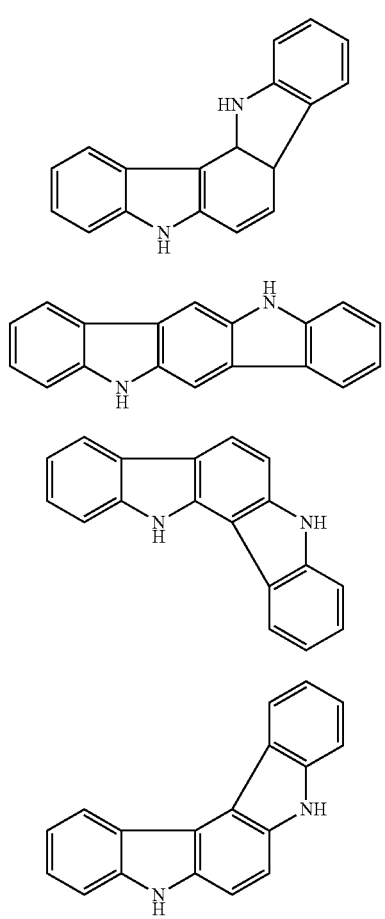

(9)

(10)

(11)

(12)

(13)

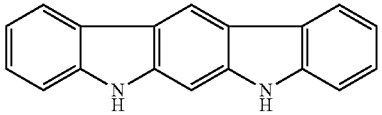

(14)

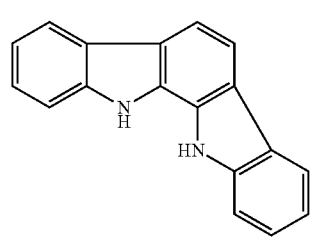

Ring A may include at least one nitrogen atom.

BRIEF DESCRIPTION OF THE DRAWINGS

Features will become apparent to those of skill in the art by describing in detail exemplary embodiments with reference to the attached drawing in which:

FIG. 1 is a schematic cross-sectional view illustrating an organic EL device according to an example embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art. In the drawing FIGURE, the dimensions of layers and regions may be exaggerated for clarity of illustration. Like reference numerals refer to like elements throughout.

According to an example embodiment, an organic EL device includes a hole transport material, in which a heterocyclic substituent is introduced in N-(azaaryl)indolocarbazole, and fluorene, dibenzofuran, or dibenzothiophene is introduced in triethylamine. The organic EL device including the hole transport material according to an embodiment may have high efficiency and long life.

According to an example embodiment, a hole transport material for an organic EL device is an amine derivative represented by compound (15) of the following Formula 5. The hole transport material may include indolocarbazole substituted with an azaaryl substituent and arylamine having a heterocycle.

[Formula 15]

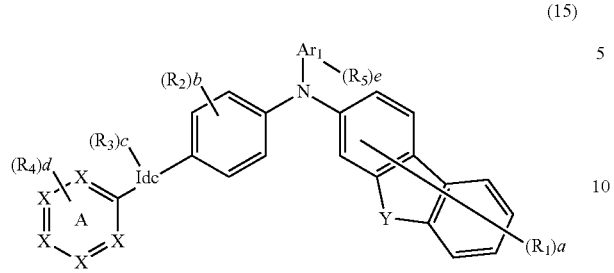

(15)

According to the present example embodiment, in compound (15), Idc is an indolocarbazole divalent group, X is a methine group or a nitrogen atom, Y is a methylene group, an oxygen atom, or a sulfur atom, Ar1 is an aryl group having 6 to 20 carbon atoms, each of $R_1$-$R_5$ independently represents a substituted or unsubstituted alkyl group of a straight or branched chain having 6 to 20 carbon atoms, or an aryl group or a heteroaryl group having 6 to 20 carbon atoms, a is an integer of 0 to 9, b is an integer of 0 to 4, c is an integer of 0 to 10, d is an integer of 0 to 5, and e is an integer of 0 to 10.

According to an example embodiment, six isomers are known as the indolocarbazole, and Idc may be selected from compounds (16) to (21) of the following Formula 6,

[Formula 6]

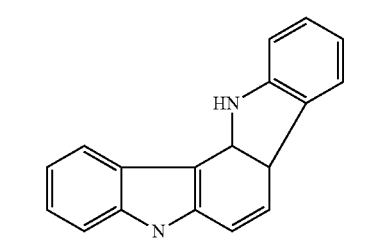

(16)

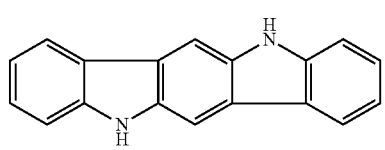

(17)

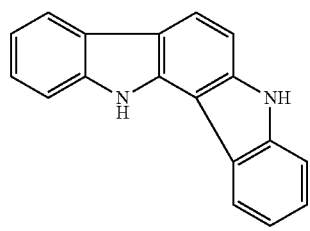

(18)

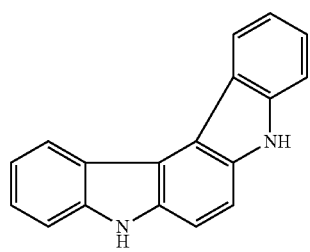

(19)

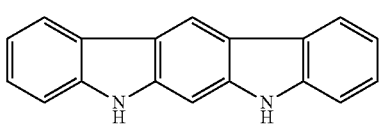

(20)

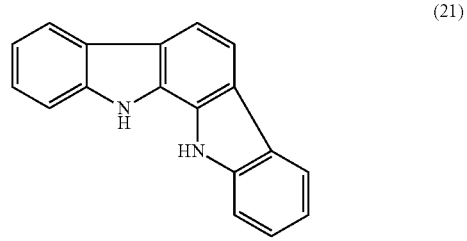

(21)

In the hole transport material for the organic EL device according to an example embodiment, ring A of N-(azaaryl) indolocarbazole includes at least one nitrogen atom. In an example embodiment, three or less nitrogen atoms may be included in the ring A. In an example embodiment, in ring A, N may be arranged so as not to form a direct bond.

In a hole transport material for an organic EL device according to an example embodiment having the above-described structures, electron affinity may be increased, and carrier transport properties may be improved. In addition, the durability with respect to electrons not used for light emission but introducing into a hole transport layer may be improved. The life of the organic EL device may be increased.

The hole transport material for the organic EL device according to an example embodiment includes an arylamine having a heterocycle. The hole transport material for the organic EL device according to an example embodiment includes carbazole as the heterocycle. In an example embodiment, in compound (15), Y is a methylene group, an oxygen atom, or a sulfur atom. Thus, the hole transport material for the organic EL device according to an embodiment may includes fluorene, dibenzofuran, or dibenzothiophene. in the hole transport material for the organic EL device according to an example embodiment having the above-described structures, electron affinity may be increased, and the durability with respect to electrons not used for light emission but introducing into a hole transport layer may be improved.

According to an example embodiment, in compound (15), each of $R_1$-$R_5$ independently represents a substituted or unsubstituted alkyl group of a straight or branched chain having 6 to 20 carbon atoms, or an aryl group or a heteroaryl group having 6 to 20 carbon atoms, a is an integer of 0 to 9, b is an integer of 0 to 4, c is an integer of 0 to 10, d is an integer of 0 to 5, and e is an integer of 0 to 10. Each of $R_1$-$R_5$ may be introduced by the number of a to e at optional and replaceable sites of the arylamine compound.

Hole transport materials for the organic EL device according to example embodiments may be represented by the following Formula 7,

[Formula 7]
(22)
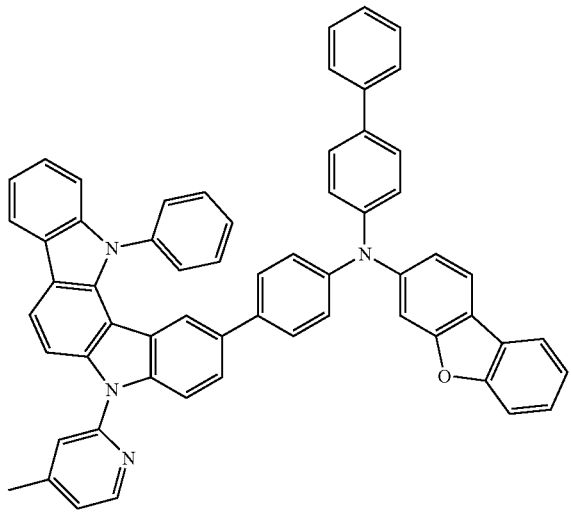
(23)
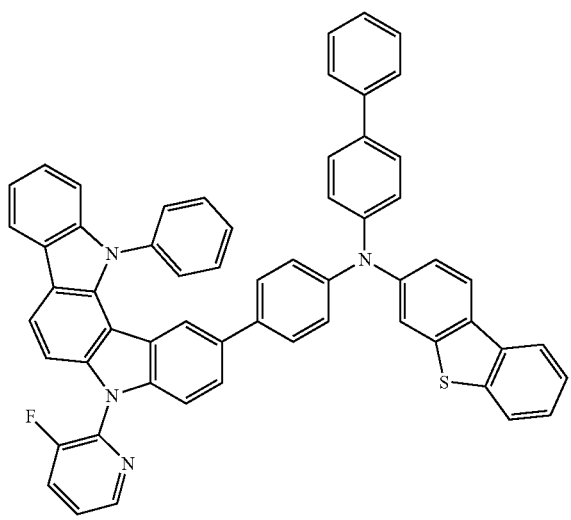
(24)
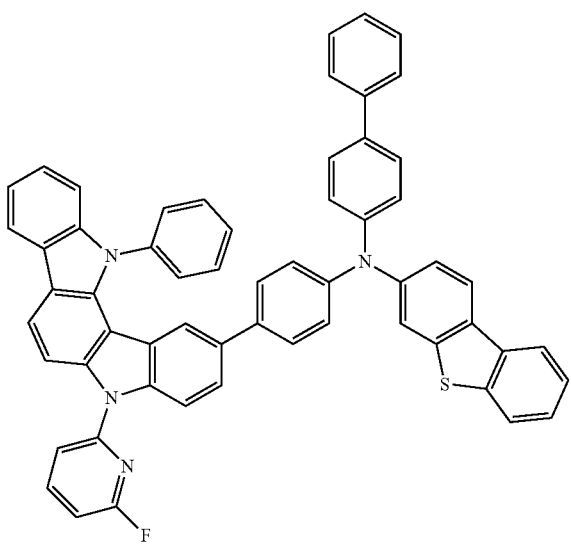
(25)
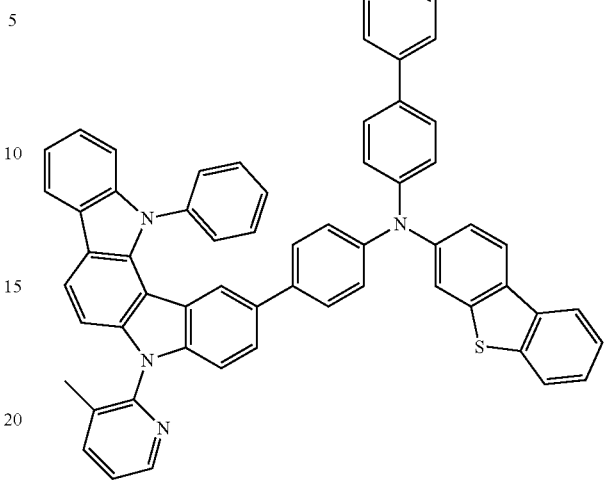
(26)
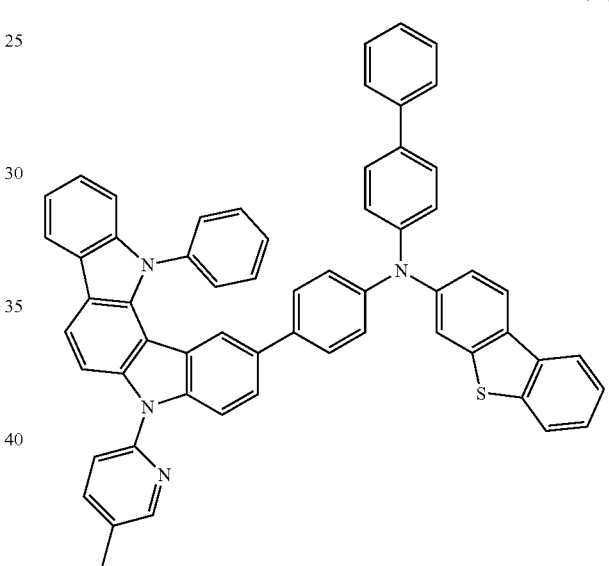
(27)
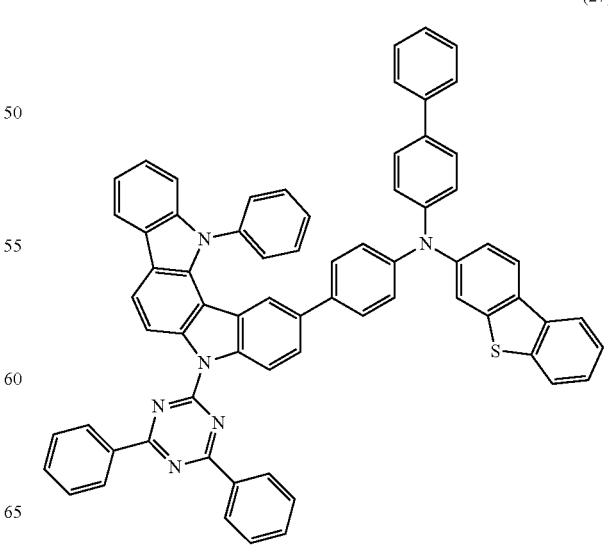

(28)
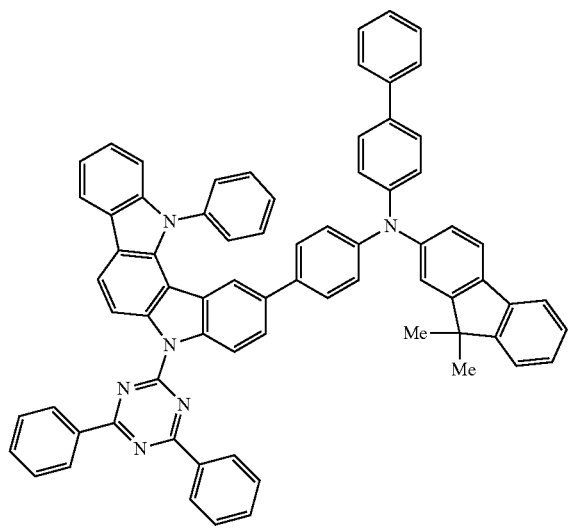
(31)
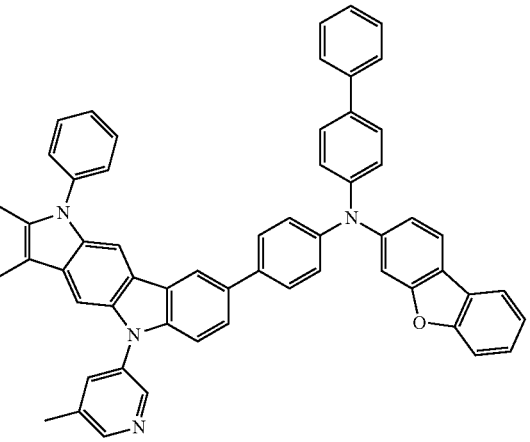
Hole transport materials for the organic EL device according to example embodiments may be represented by the following Formula 8,
[Formula 8]
(29)
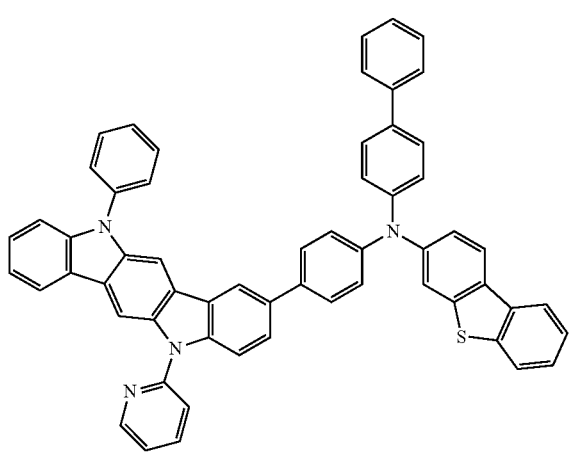
(32)
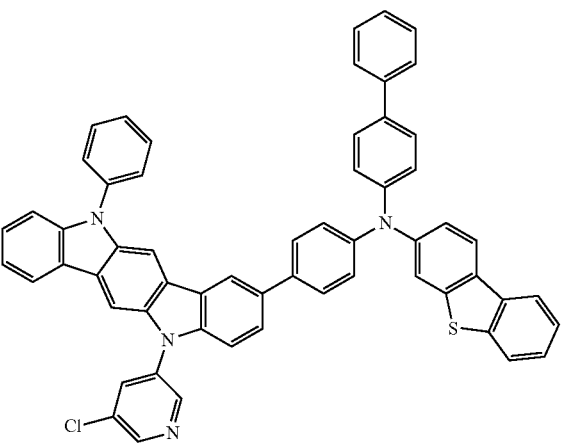
(30)
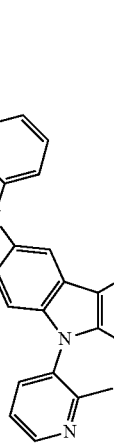
(33)
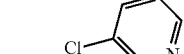

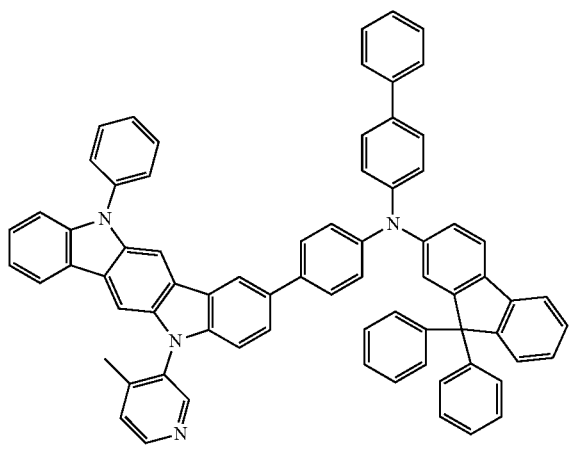
(34)
Hole transport materials for the organic EL device according to example embodiments may be represented by the following Formula 9,
[Formula 9]
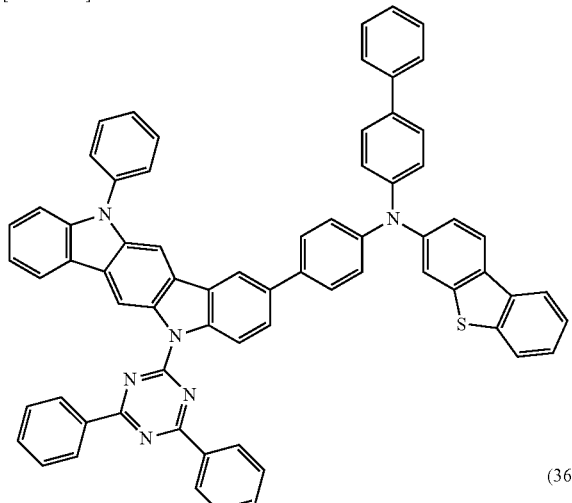
(35)
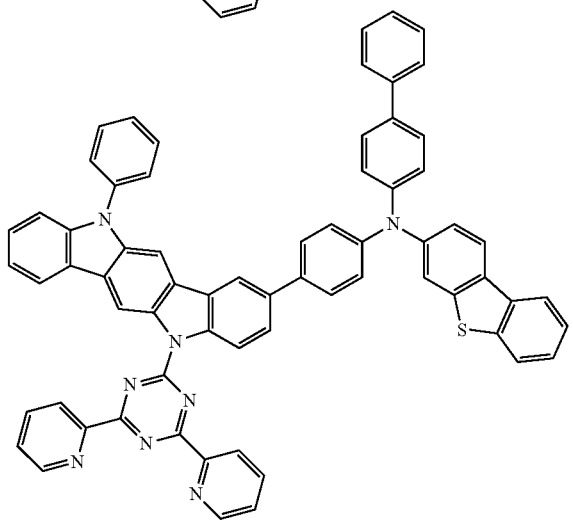
(36)
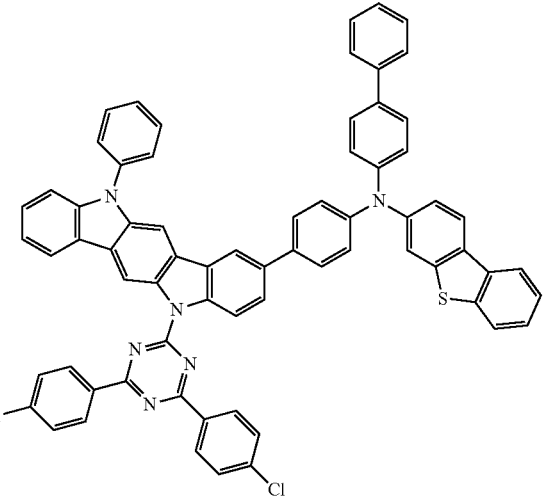
(37)
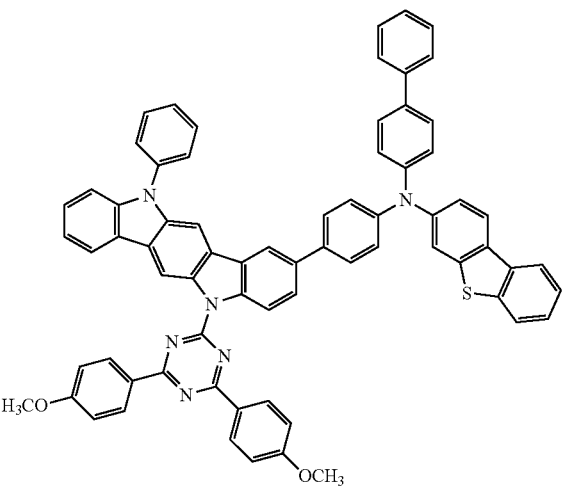
(38)
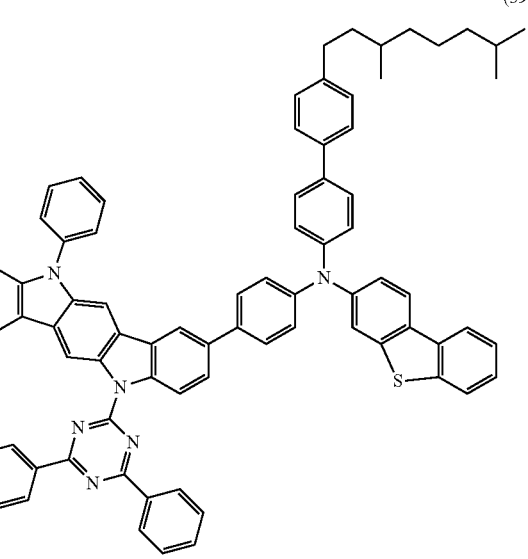
(39)
The hole transport material for the organic EL device according to example embodiments may have the above-described structures. Such materials may be used to form a hole transport layer having high efficiency and long life in an organic EL device. According to an example embodiment, the hole transport material for the organic EL device includes N-(azaaryl)indolocarbazole and triethylamine portion including fluorene, dibenzofuran, or dibenzothiophene, and carrier transport properties may be improved. In addition, an organic EL device possibly driven by a low voltage may be manufactured, and the durability with respect to electrons not used for light emission but introduced to a hole transport layer and life may be improved. The hole transport material for the organic EL device according to example embodiments may have the above-described structures, and the stability with respect to carriers may be improved, and an organic EL device having long life may be manufactured.

Organic EL Device

An organic EL device using the hole transport material for the organic EL device according to an example embodiment will now be described.

FIG. 1 is a schematic diagram illustrating an embodiment of an organic EL device 100 according to an example embodiment.

According to the present example embodiment, an organic EL device 100 may include, for example, a substrate 102, a positive electrode 104, a hole injection layer 106, a hole transport layer 108, an emission layer 110, an electron transport layer 112, an electron injection layer 114, and a negative electrode 116.

The substrate 102 may be, for example, a transparent glass substrate, or a flexible substrate of a semiconductor substrate resin including silicon. Methods for forming organic thin layers may include a vacuum deposition method or various coating methods. The positive electrode 104 is disposed on the substrate 102, and may be formed by using indium tin oxide (ITO) or indium zinc oxide (IZO). The hole injection layer 106 is disposed on the positive electrode 104, and may include, for example, 4,4',4''-tris(N-1-naphthyl-N-phenylamino)triphenylamine (1-TNATA), 4,4'-bis(N,N-di(3-tolyl)amino)-3,3-dimethylbiphenyl (HMTPO), and the like. The hole transport layer 108 is disposed on the hole injection layer 106 and may be formed by using the hole transport material for the organic EL device according to an example embodiment. The emission layer 110 is disposed on the hole transport layer 108 and may be formed by doping tetra-t-butylperylene (TBP) into a host material including 9,10-di-(2-naphthyl)anthracene (ADN). The electron transport layer 112 is disposed on the emission layer 110 and may be formed by using a material including, for example, tris(8-hydroxyquinolinato)aluminum (Alq3). The electron injection layer 114 is disposed on the electron transport layer 112 and may be formed by using a material including, for example, lithium fluoride (LiF). The negative electrode 116 is disposed on the electron injection layer 114, and is formed by using a metal such as Al or a transparent material such as ITO or IZO. The thin layers may be formed by using an appropriate film forming method according to the materials, such as a vacuum deposition method, a sputtering method, or various coating methods.

In the organic EL device 100 according to the present example embodiment, the hole transport material for the organic EL device according to an embodiment is used, and a hole transport layer having high efficiency and long life may be formed. The hole transport material for the organic EL device according to an embodiment may be applied in an organic EL light-emitting apparatus of an active matrix using a thin film transistor (TFT).

EXAMPLES

Synthetic Methods

A hole transport material for the organic EL device according to an embodiment may be synthesized by, for example, the following Formula 10,

[Formula 10]

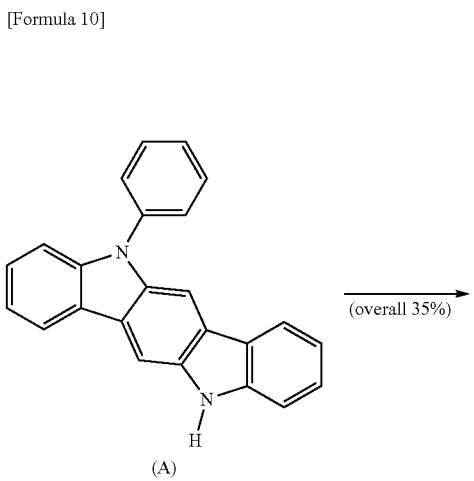

(A)

-continued
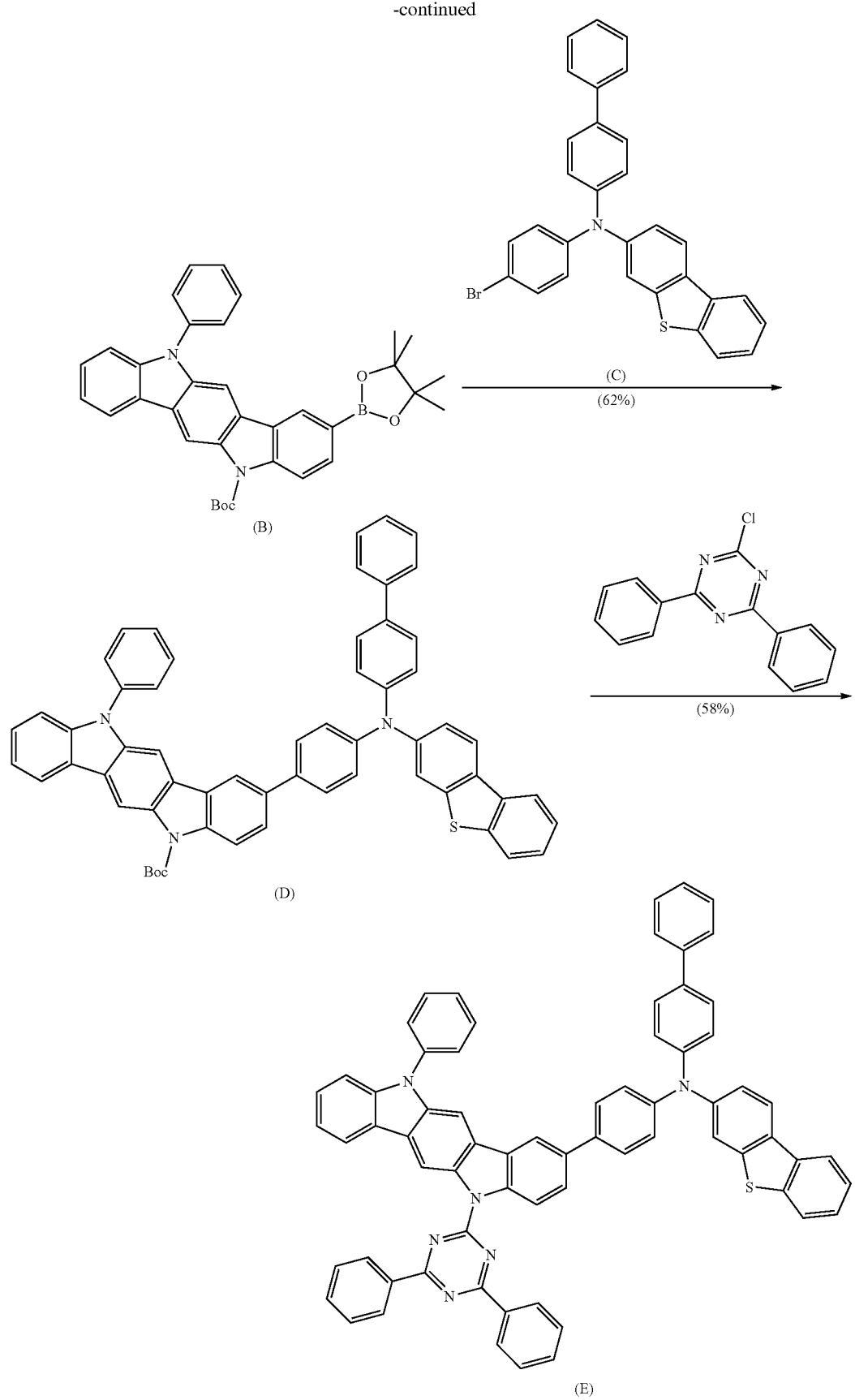

Synthesis of Indolocarbazole Boronic Acid Pinacol Ester (Compound B)

5.82 g (17.5 mmol) of indolocarbazole (Compound A) was added into 200 ml of N,N-dimethylformamide, and 30 ml of an N,N-dimethylformamide solution of 3.43 g (19.2 mmol) of N-bromosuccinimide was added drop by drop for 15 minutes under a nitrogen gas atmosphere while cooling using ice. The temperature was increased to room temperature while stirring, and the stirring was performed for 5 hours. The reactant was poured into water, and extracted using chloroform-hexane three times. An organic layer was washed using water and a saturated saline solution, and dried using anhydrous magnesium sulfate. After filtering, the filtrate was concentrated to obtain a concentrated residue.

The concentrated residue was added into 300 ml of tetrahydrofuran, and a nitrogen gas was substituted under a nitrogen reaction atmosphere. While stirring, 5.84 g (57.8 mmol) of triethylamine, and 428 mg (3.50 mmol) of 4-dimethylaminopyridine were added. While cooling using ice, a 50 ml of tetrahydrofuran solution of 8.40 g (38.5 mmol) of di-t-butyl dicarbonate was added drop by drop for 10 minutes. The temperature was increased to room temperature while stirring, and the stirring was continued at 50° C. for 6 hours. The reactant was poured into water and extracted using chloroform three times. An organic layer was washed using water and a saturated saline solution and dried using anhydrous magnesium sulfate. The product was filtered using a celite-silica gel, and the filtrate was concentrated to obtain a concentrated product. The concentrated product was dissolved in toluene and concentrated under a reduced pressure, and these processes were performed three times. The product thus obtained was dissolved in 100 ml of tetrahydrofuran under a nitrogen gas atmosphere and cooled in a dry ice-acetone bath. Into the reactant, 12.0 ml (1.6 M in hexane, 19.2 mmol) of n-butyl lithium was added drop by drop for 10 minutes, and stirred at the same temperature for 1 hour. Into the reactant, 4.88 g (26.2 mmol) of 4,4,5,5-tetramethyl-2-isopropoxy-1,3,2-dioxaborolane was injected, the temperature was increased to room temperature while stirring, and the stirring was continued at room temperature for 2 hours. Into the reactant, water was added, and extraction was performed using chloroform three times. An organic layer was washed using water and a saturated saline solution and dried using anhydrous magnesium sulfate. After filtering, the filtrate was concentrated, and the residue was purified by means of a silica gel chromatography (cyclohexane/toluene=10/1→2/1) to obtain 3.42 g (6.12 mmol, overall 35%) of indolocarbazole boronic acid pinacol ester (Compound B).

Synthesis of Coupling Compound (Compound D)

4.41 g (7.90 mmol) of indolocarbazole boronic acid pinacol ester (Compound B), and 4.40 g (8.68 mmol) of bromoarylamine (Compound C) were added into a mixture of 200 ml of toluene, 200 ml of dioxane, and 100 ml of 2 M-aqueous sodium carbonate solution. Then, 456 mg (0.395 mmol) of tetrakis(triphenylphosphine)palladium(0) was added, and the reactant was heated and refluxed under a nitrogen gas atmosphere for 8 hours while stirring. Water was added into the reactant, and extraction was performed using chloroform. An organic layer was washed using water and a saturated saline solution in order and dried using anhydrous magnesium sulfate. The organic layer thus obtained was filtered, concentrated, and purified by means of a flash chromatography (cyclohexane/toluene=5/1→1/1) to obtain 4.20 g (4.90 mmol, yield 62%) of a coupling compound (Compound D).

Synthesis of Compound E 2.58 g (4.62 mmol) of the coupling compound (Compound D) was added into 100 ml of methylene chloride, and 50 ml of trifluoroacetic acid was added drop by drop for 15 minutes under a nitrogen gas atmosphere while cooling using ice. The reactant was stirred for 1 hour, and trifluoroacetic acid was distilled with a solvent under a reduced pressure. Into the residue, 100 ml of toluene was added and then concentrated for three times. The residue thus obtained was dissolved in 200 ml of tetrahydrofuran. Into another reaction vessel, 100 ml of a tetrahydrofuran dispersion of 277 mg (60% in oil, 6.93 mmol) of sodium hydride was prepared, and 1.23 g (4.62 mmol) of 2-chloro-4,6-diphenyl-1,3,5-triazine was added while stirring with ice-cooling. Then, the tetrahydrofuran solution including the residue was added drop by drop for 15 minutes. The temperature was increased to room temperature while stirring, and then the stirring was continued at 50° C. for 6 hours. Immediately after the reaction, 5 ml of isopropyl alcohol was added into the reactant, and water was added. Extraction was performed using chloroform. An organic layer was washed using water and a saturated saline solution in order and dried using anhydrous magnesium sulfate. The organic layer thus obtained was filtered, concentrated, and purified by means of a flash chromatography (cyclohexane/toluene=5/1→1/1) to obtain 2.65 g (2.68 mmol, yield 58%) of Compound E.

The identification of the synthesized compounds was performed by mass spectrum measurement.

Through the above-described preparation methods, the compound of Example 1 was obtained. In addition, the compounds of Comparative Examples 1 to 3 were prepared for comparison. The compounds of Example 1 and Comparative Examples 1 to 3 are shown in the following Formula 11.

[Formula 11]

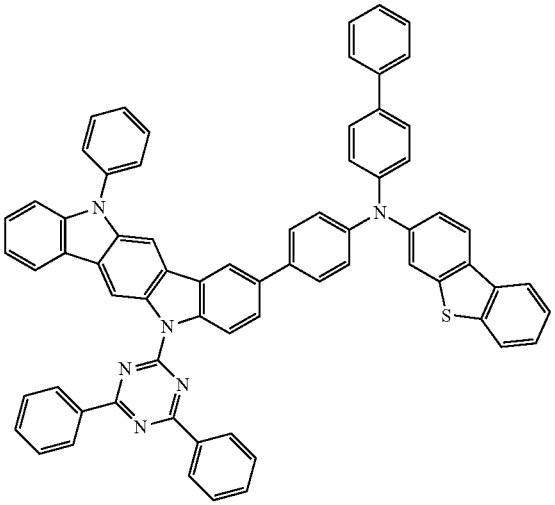

Example 1

-continued

Comparative Example 1

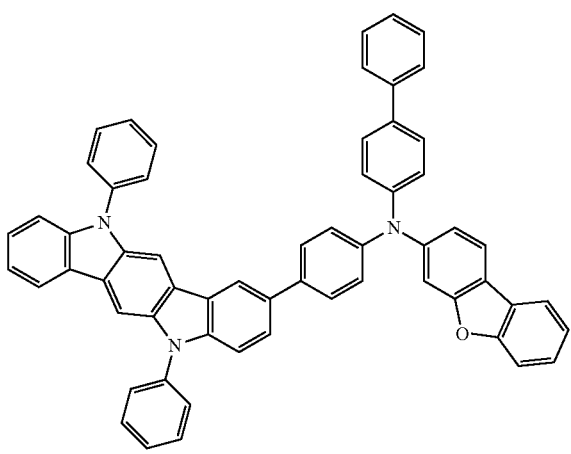

Comparative Example 2

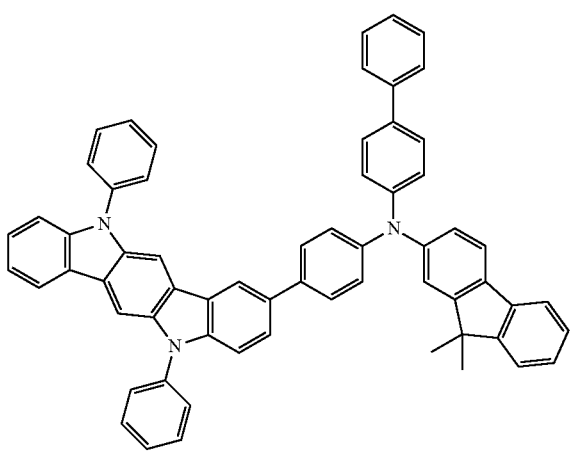

Comparative Example 3

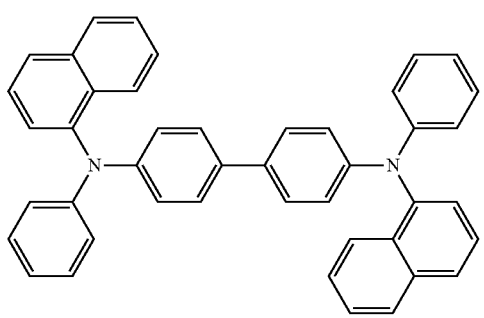

Organic EL devices were manufactured by using the compounds of Example 1 and Comparative Examples 1 to 3 as hole transport materials. Transparent glass substrate was used as the substrate 102, and the positive electrode 104 was formed using ITO in a thickness of about 150 nm. The hole injection layer 106 was formed using HMTPD in a thickness of about 60 nm, and the hole transport layer 108 was formed in a thickness of about 30 nm. The emission layer 110 was formed by using a layer obtained by doping 3% TBP into ADN having a thickness of about 25 nm. The electron transport layer 112 was formed using Alq3 in a thickness of about 25 nm, and the electron injection layer 114 was formed using LiF in a thickness of about 1 nm. The negative electrode 116 was formed using Al in a thickness of about 100 nm.

With respect to the organic EL devices thus manufactured, voltage, current efficiency, and half-life were evaluated. The current efficiency is obtained at 10 mA/cm$^2$; the half-life means luminance half-life from the initial luminance of about 1,000 cd/m$^2$. The evaluation results are illustrated in the following Table 1.

TABLE 1

| | Voltage (V) | Current efficiency (cd/A) | Half-life (hr) |
|---|---|---|---|
| Example 1 | 6.3 | 6.5 | 3,150 |
| Comparative Example 1 | 6.8 | 6.0 | 2,150 |
| Comparative Example 2 | 7.0 | 5.8 | 1,800 |
| Comparative Example 3 | 8.0 | 5.3 | 1,200 |

As shown in Table 1, the compound of Example 1 was used to form an organic EL device operated by a lower voltage when compared to the compounds of Comparative Examples 1 to 3. On the current efficiency, the compound of Example 1 attained higher current efficiency than the compounds of Comparative Examples 1 to 3. With respect to the half-life, the compound of Example 1 exhibited longer life than the compounds of Comparative Examples 1 to 3. Without being bound by theory, it is believed that, when examining Comparative Example 1 and Comparative Example 2, in Comparative Example 1, electron affinity was improved, and the durability with respect to electrons not used for emitting light but reaching a hole transport layer was improved by introducing a heterocycle such as dibenzofuran at a triarylamine portion. In Example 1, it was thought that electron affinity was even further improved, and the durability with respect to electrons not used for emitting light but reaching a hole transport layer was improved, and the life of an organic EL device was increased by introducing a heterocycle such as triazine at the N-(azaaryl)indolocarbazole portion.

By way of summation and review, an example of a light-emitting device (herein referred to as an organic EL device) known in the art is an organic EL device which includes a positive electrode, a hole transport layer disposed on the positive electrode, an emission layer disposed on the hole transport layer, an electron transport layer disposed on the emission layer, and a negative electrode disposed on the electron transport layer. Holes injected from the positive electrode are injected into the emission layer via the hole transport layer. Meanwhile, electrons are injected from the negative electrode, and then injected into the emission layer via the electron transport layer. The holes and the electrons injected into the emission layer are recombined to generate excitons within the emission layer. The organic EL device emits a light by using a light generated by radiation and deactivation of the excitons. The above-described configuration of the organic EL device is an example; it may be changed in various forms.

Improved charge transport properties and durability of electrons introduced to a hole transport layer may help in the manufacture an organic EL device having high efficiency and long life. In application of the organic EL device to a display apparatus, high efficiency and long life of the organic EL device are desirable, and for realizing the high efficiency and long life, normalization, stabilization and durability of the hole transport layer are considered.

As described above, embodiments relate to a hole transport material, which may provide a hole transport layer and an organic EL device having high efficiency and long life, and an organic electroluminescence device using the same. In the hole transport material for the organic EL device according to an embodiment, a heterocycle substituent may be introduced in N-(azaaryl)indolocarbazole, and fluorene, dibenzofuran, or dibenzothiophene may be introduced in triarylamine, and electron affinity and durability with respect to electrons not emitting light but reaching a hole transport layer may be improved. Using the hole transport material for the organic EL device according to an example embodiment, the stability of the hole transport material may be improved, and driving at a low voltage and a long life of an organic EL device may be realized. The hole transport material for the organic EL device according to an example embodiment includes at least one nitrogen atom in N-(azaaryl)indolocarbazole, and electron affinity and durability with respect to electrons not emitting light but reaching a hole transport layer may be improved, and the life of an organic EL device may be increased. In an organic EL device according to an example embodiment, a hole transport layer may be formed by using a hole transport material for an organic EL device, in which a heterocycle substituent is introduced in N-(azaaryl)indolo-carbazole, and fluorene, dibenzofuran, or dibenzothiophene is introduced in triarylamine, and electron affinity and durability with respect to electrons not emitting light but reaching a hole transport layer may be improved.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A hole transport material for an organic electroluminescence device, the hole transport material being a compound represented by following Formula 1:

[Formula 1]

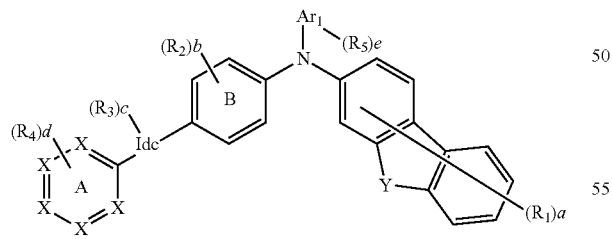

(1)

wherein, Idc is an indolocarbazole group linked to ring A and ring B, each X of ring A is independently a methine group or a nitrogen atom, at least one X of ring A being a nitrogen atom, Y is a methylene group, an oxygen atom, or a sulfur atom, Ar$_1$ is an aryl group having 6 to 20 carbon atoms, each of R$_1$-R$_5$ independently represents a substituted or unsubstituted straight or branched chain alkyl group having 6 to 20 carbon atoms, or an aryl group or a heteroaryl group having 6 to 20 carbon atoms, a is an integer of 0 to 9, b is an integer of 0 to 4, c is an integer of 0 to 10, d is an integer of 0 to 5, and e is an integer of 0 to 10.

2. The hole transport material as claimed in claim 1, wherein:

Idc is one of indolocarbazole groups (2) to (7):

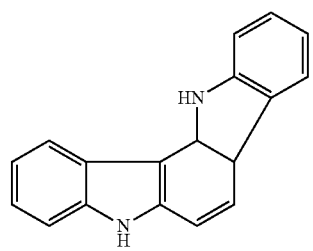

(2)

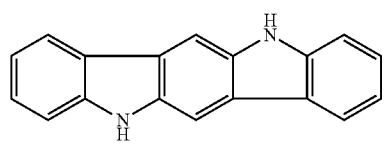

(3)

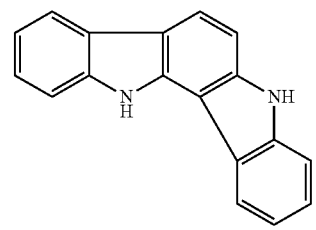

(4)

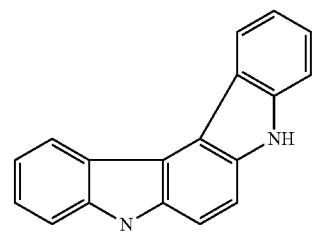

(5)

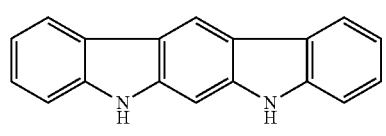

(6)

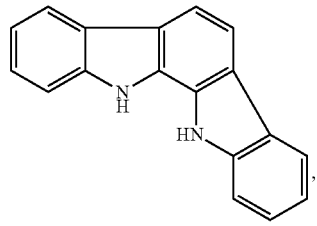

(7)

-continued (7)

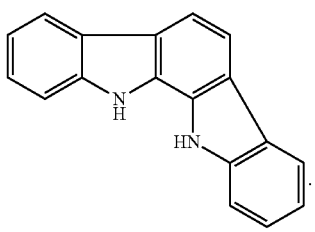

and ring B is bound to a carbon of Idc.

3. An organic electroluminescence device comprising a hole transport layer that includes a hole transport material, the hole transport material being a compound represented by the following Formula 3:

[Formula 3]

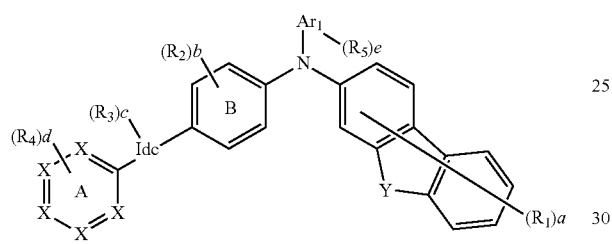

wherein, Idc is an indolocarbazole group linked to Ring A and Ring B, each X of ring A is independently a methine group or a nitrogen atom, at least one X of ring A being a nitrogen atom, Y is a methylene group, an oxygen atom, or a sulfur atom, $Ar_1$ is an aryl group having 6 to 20 carbon atoms, each of $R_1$-$R_5$ independently represents a substituted or unsubstituted straight or branched chain alkyl group having 6 to 20 carbon atoms, or an aryl group or a heteroaryl group having 6 to 20 carbon atoms, a is an integer of 0 to 9, b is an integer of 0 to 4, c is an integer of 0 to 10, d is an integer of 0 to 5, and e is an integer of 0 to 10.

4. The organic electroluminescence device as claimed in claim 3, wherein:

Idc is one of indolocarbazole groups (9) to (14):

(9)

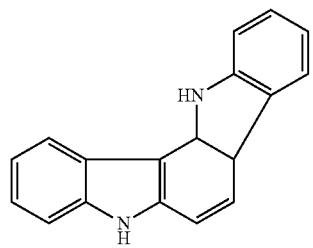

-continued (10)

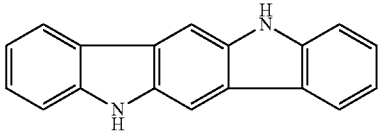

(11)

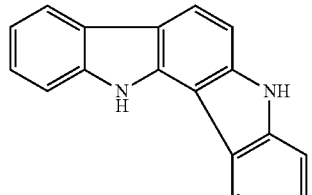

(12)

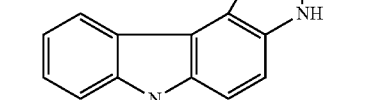

(13)

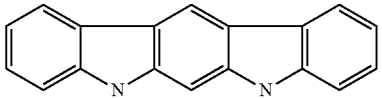

(14)

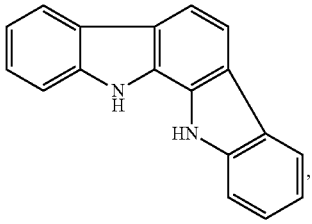

and ring B is bound to a carbon of Idc.

5. A hole transport material for an organic electroluminescence device, wherein the hole transport material is represented by one of compounds (22) to (39):

(22)

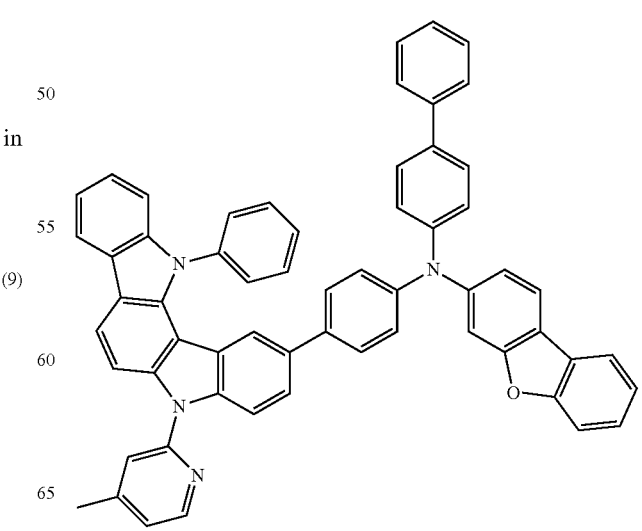

(23)
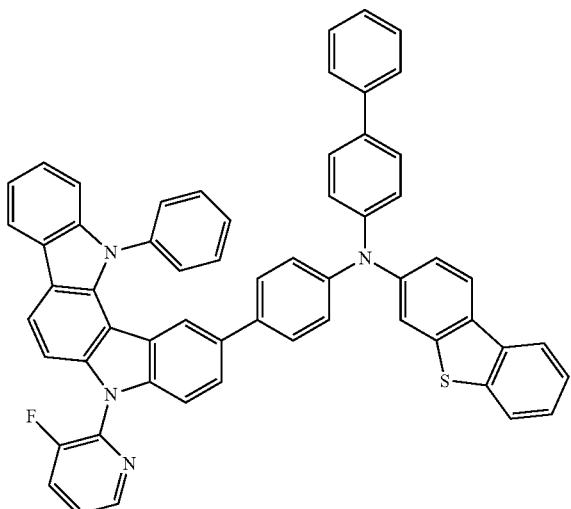
(24)
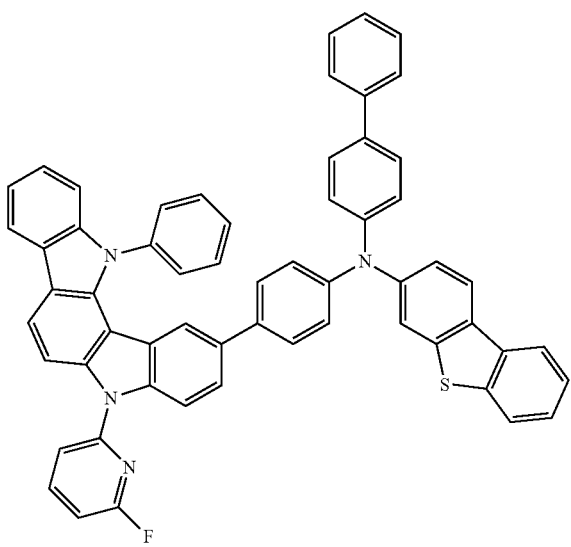
(25)
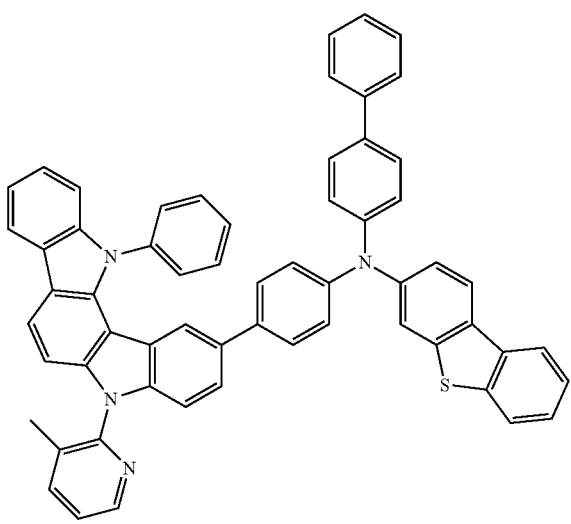
(26)
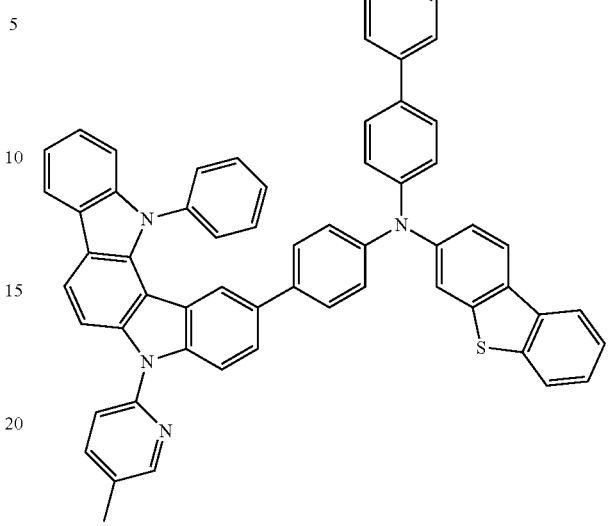
(27)
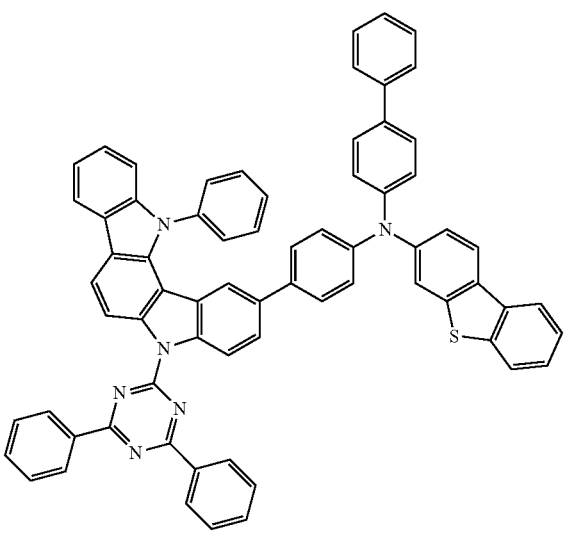
(28)
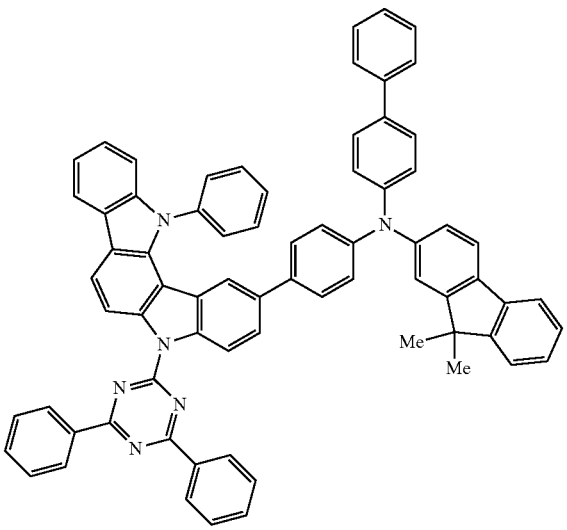

(29)
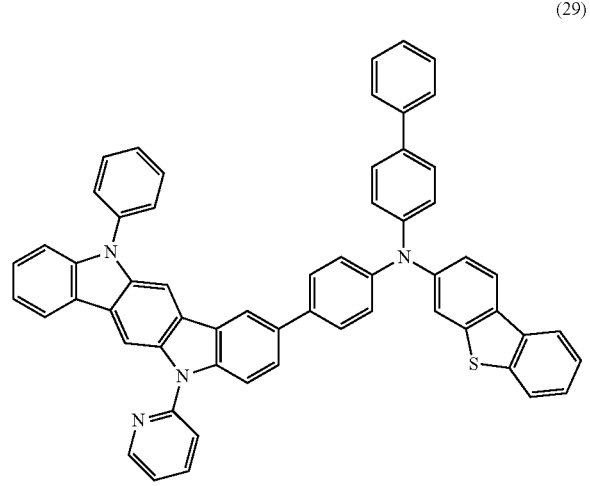
(32)
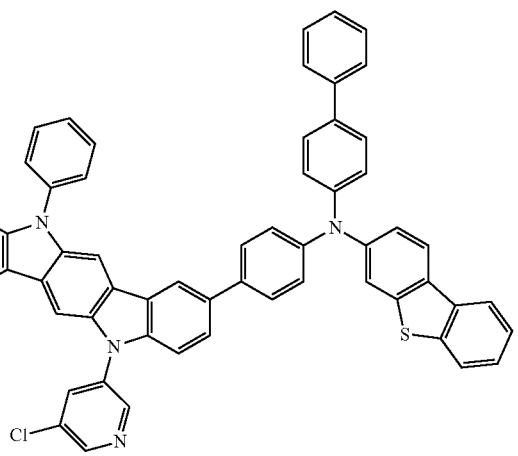
(30)
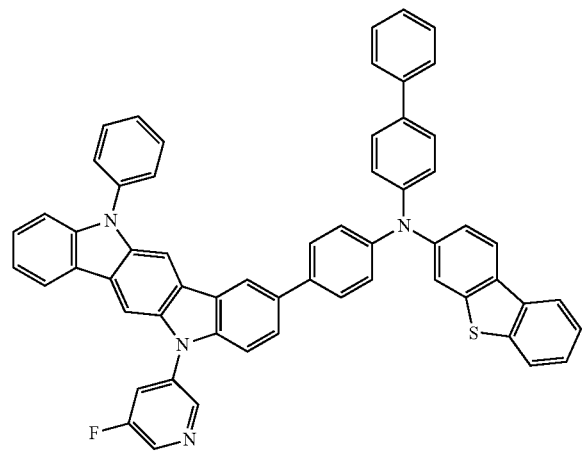
(33)
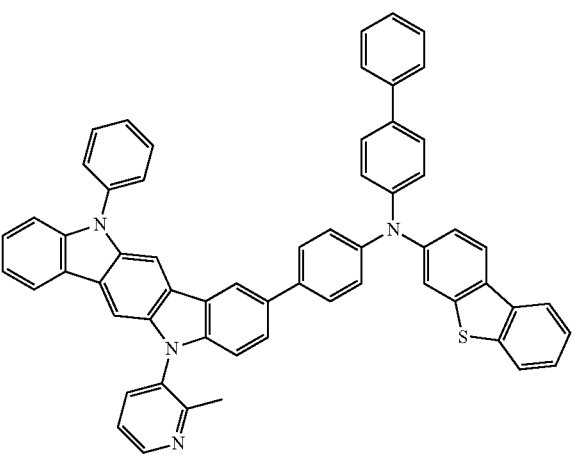
(31)
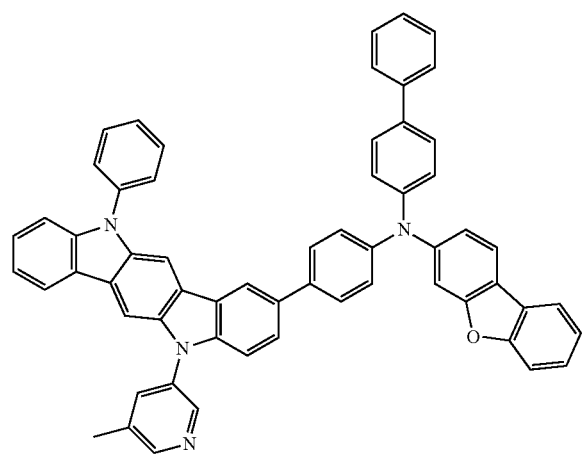
(34)
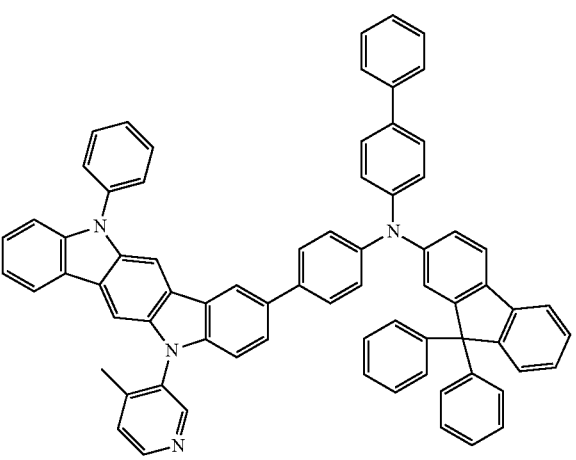

(35)
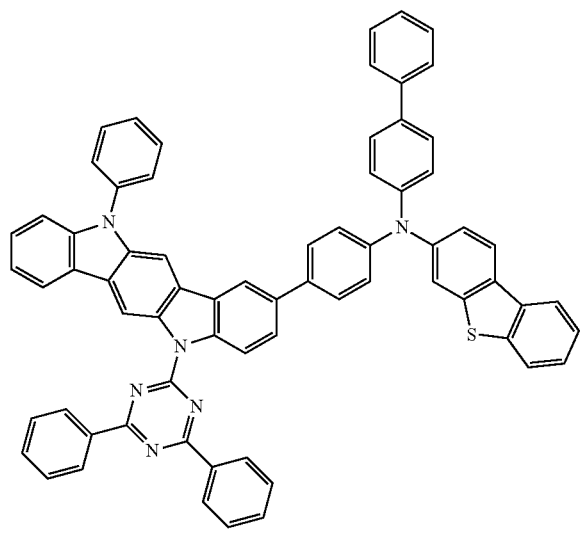
(36)
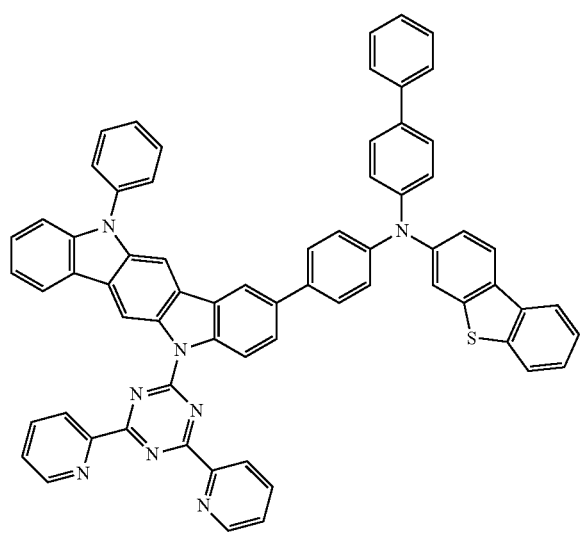
(37)
(38)
(39)
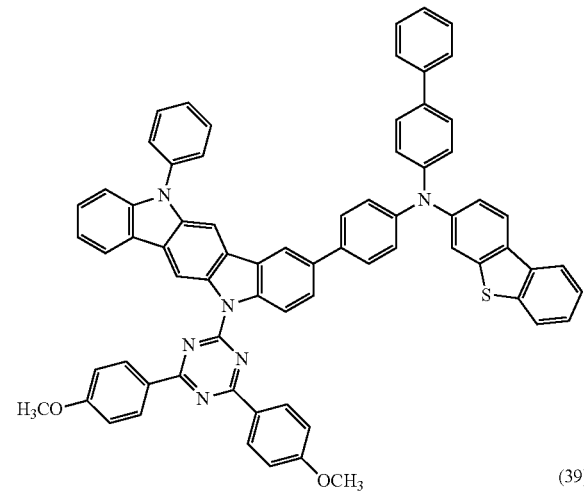
6. An organic electroluminescence device comprising a hole transport layer that includes a hole transport material, wherein the hole transport material is represented by one of compounds (22) to (39):
(22)
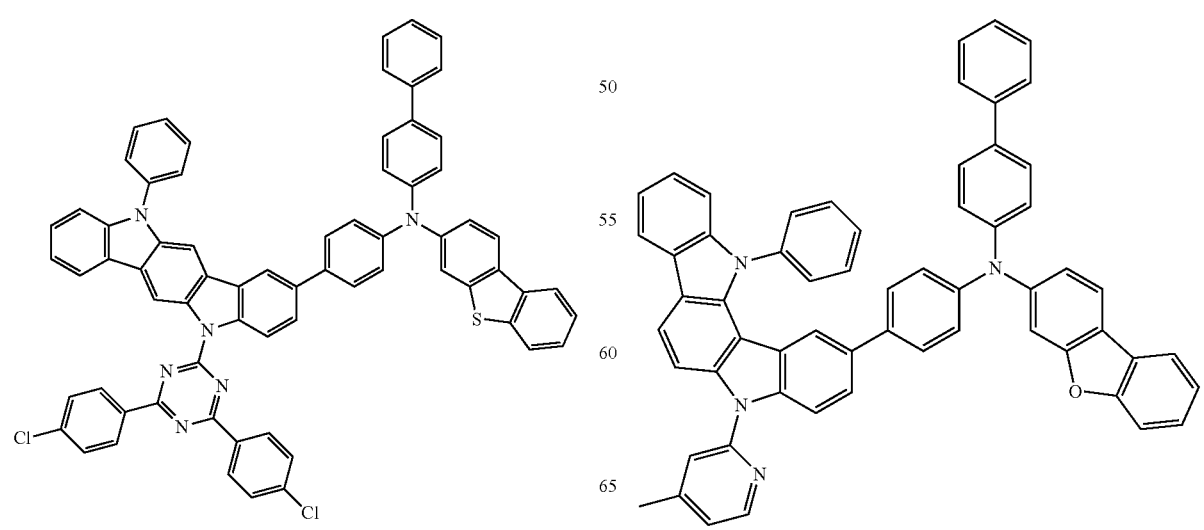

(23)
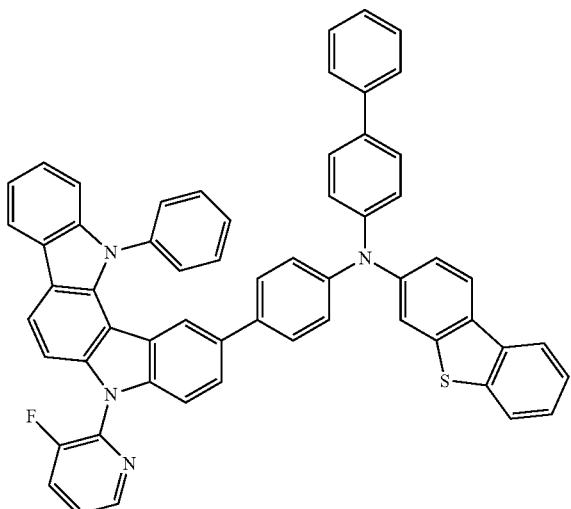
(24)
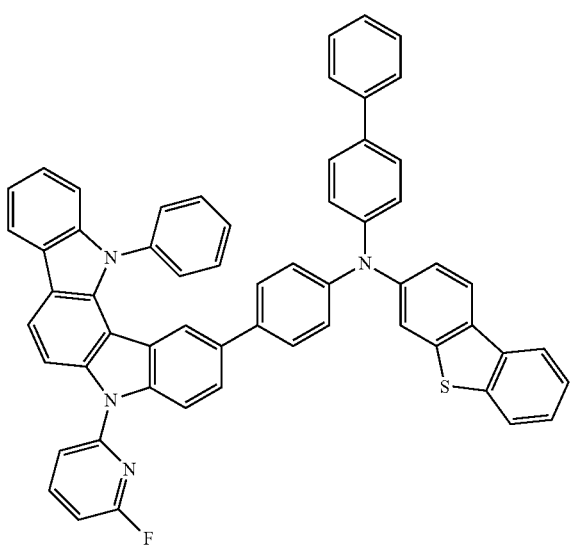
(25)
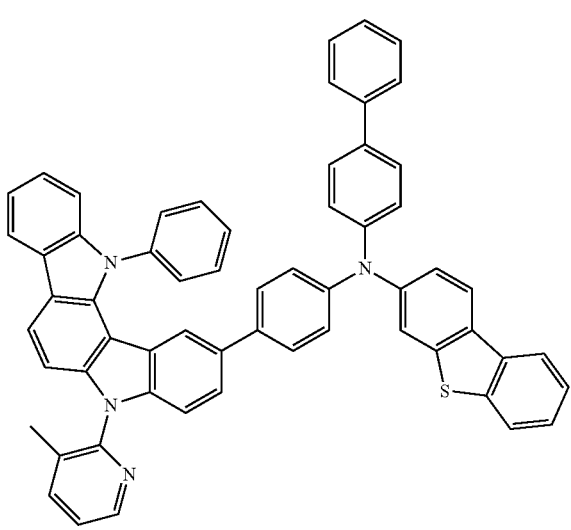
(26)
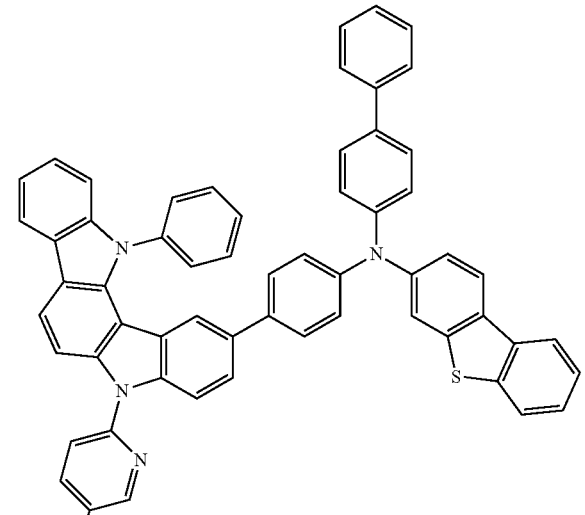
(27)
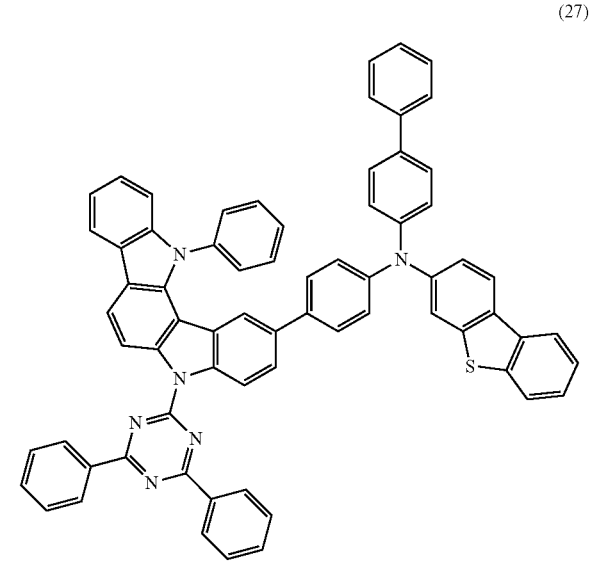 [SMILES: CC1(C)c2ccccc2-c2ccc(N(c3ccc(-c4ccccc4)cc3)c3ccc(-c4ccc5c(c4)c4c(ccc6c7ccccc7n(-c7ccccc7)c64)n5-c4nc(-c5ccccc5)nc(-c5ccccc5)n4)cc3)cc21]
(28)
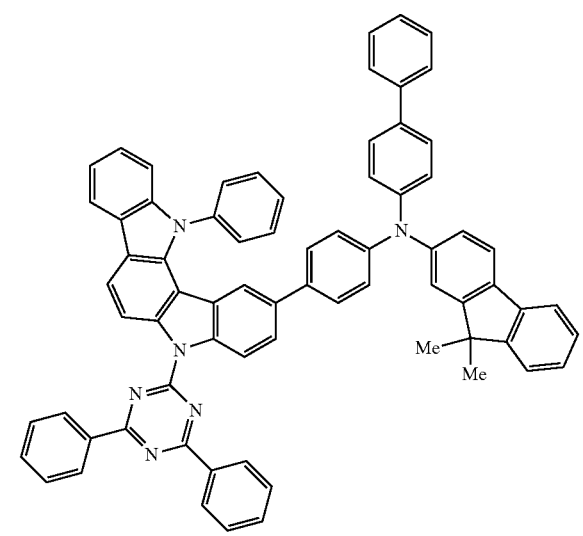

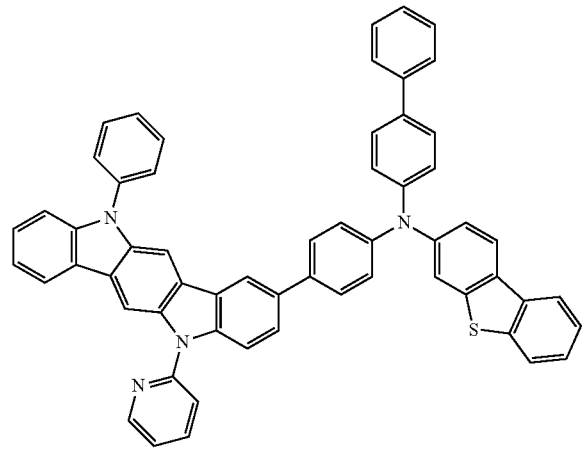
(29)
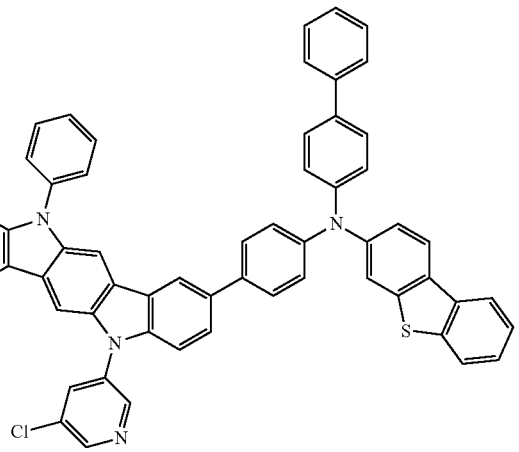
(32)
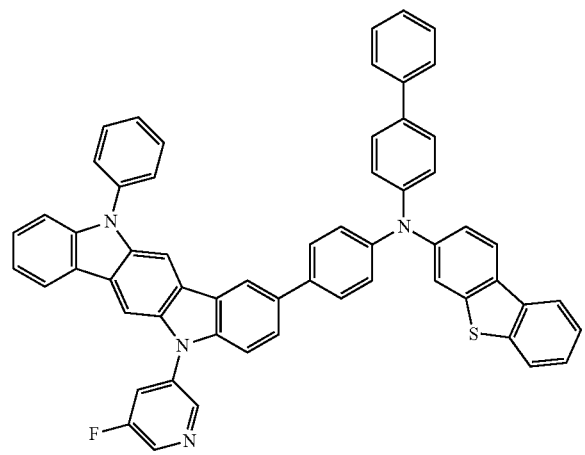
(30)
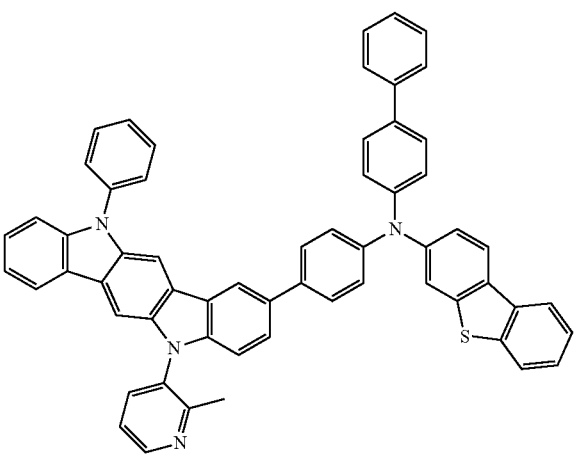
(33)
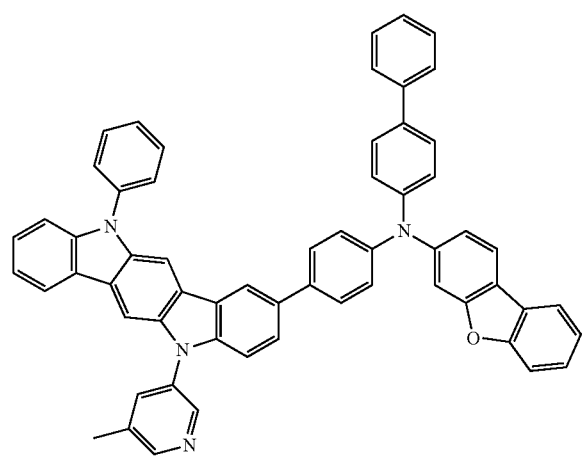
(31)
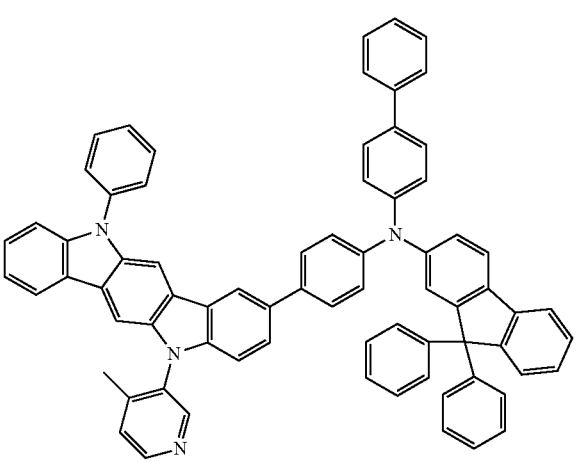
(34)

(35)
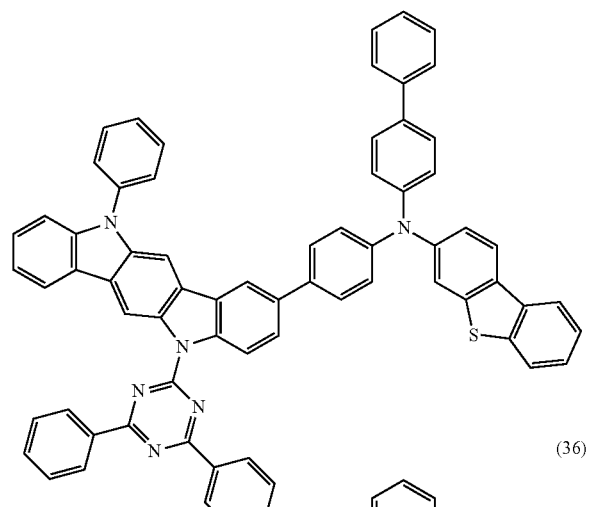
(36)
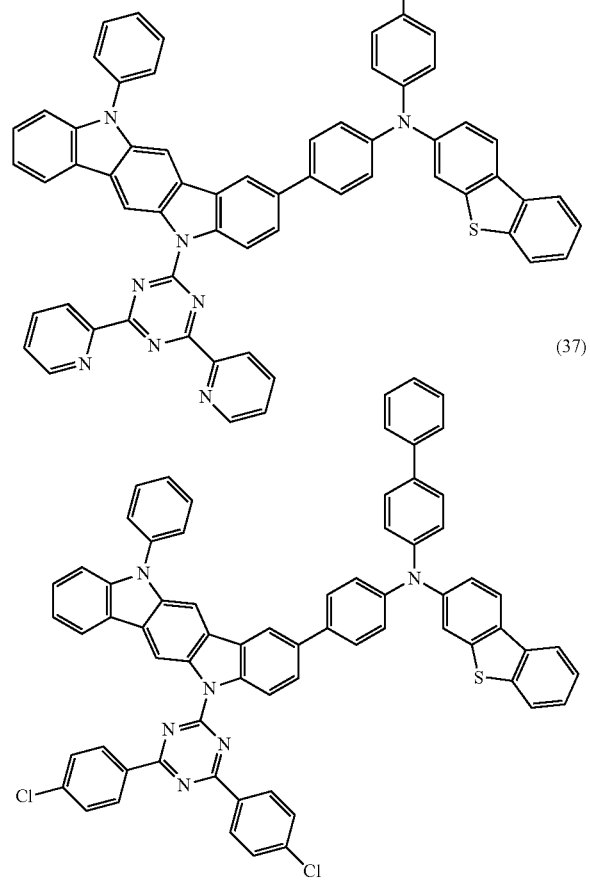
(38)
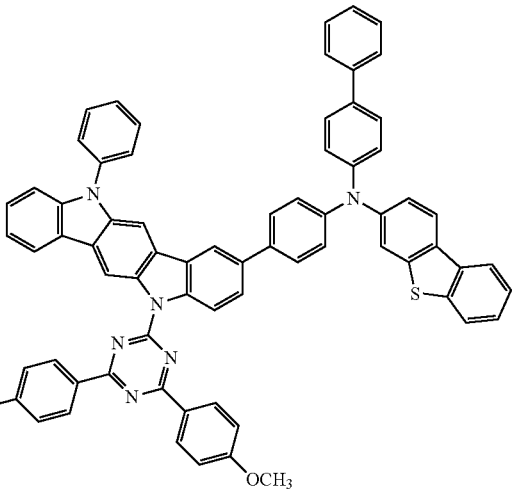
(37)
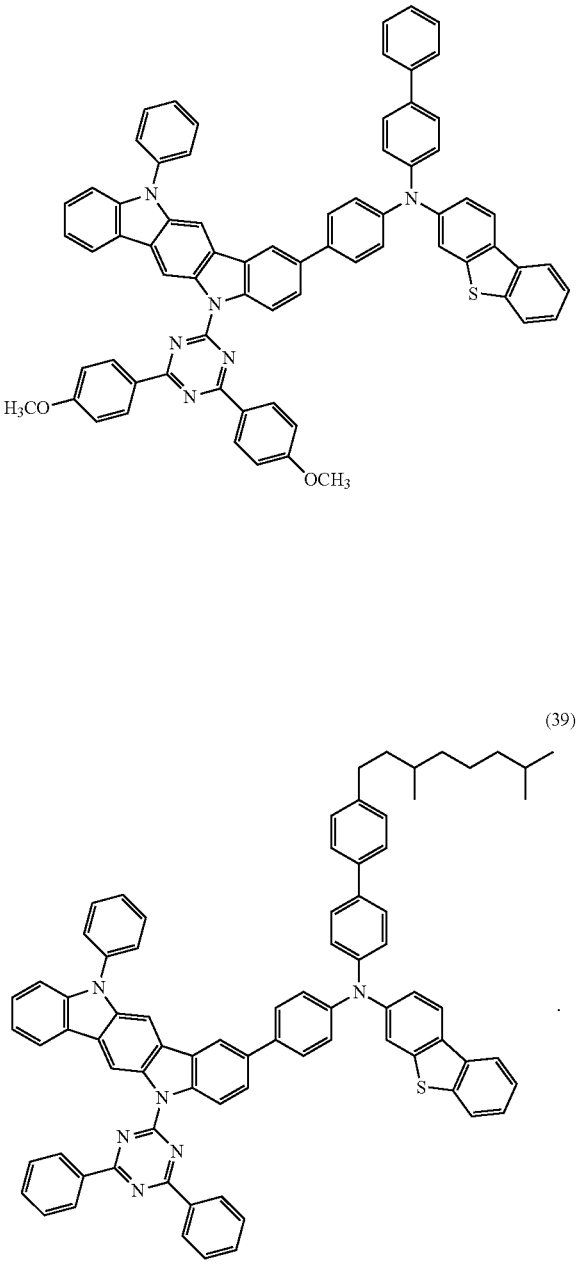
(39)
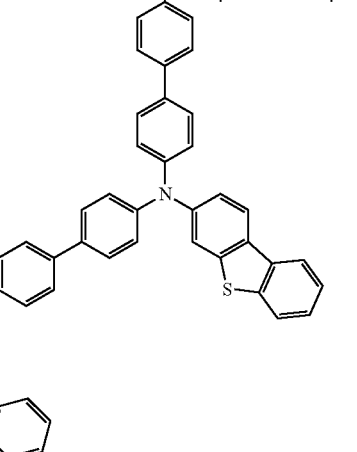
* * * * *